United States Patent [19]

Clark

[11] 4,449,746
[45] * May 22, 1984

[54] MOBILE COMPUTERIZED TOMOGRAPHY UNIT

[75] Inventor: Ronald G. Clark, Gainesville, Fla.

[73] Assignee: Synergetics, Inc., Gainesville, Fla.

[*] Notice: The portion of the term of this patent subsequent to Aug. 1, 1995 has been disclaimed.

[21] Appl. No.: 37,264

[22] Filed: May 9, 1979

Related U.S. Application Data

[63] Continuation of Ser. No. 826,527, Aug. 22, 1977, Pat. No. 4,181,347.

[51] Int. Cl.³ .................. B62D 39/00; B60P 3/00; B60P 3/32

[52] U.S. Cl. .................. 296/1 R; 296/19; 296/24 R

[58] Field of Search .................. 296/1, 19, 20, 21, 16, 296/17, 1 R, 24 R

[56] References Cited

U.S. PATENT DOCUMENTS 4,019,772  4/1977  Lee .................................. 296/20

Primary Examiner—Richard A. Bertsch
Attorney, Agent, or Firm—Hedman, Casella, Gibson, Costigan & Hoare

[57] ABSTRACT

A self-contained mobile computer tomography scanner (CT scanner) unit equipped with full support systems.

5 Claims, 5 Drawing Figures

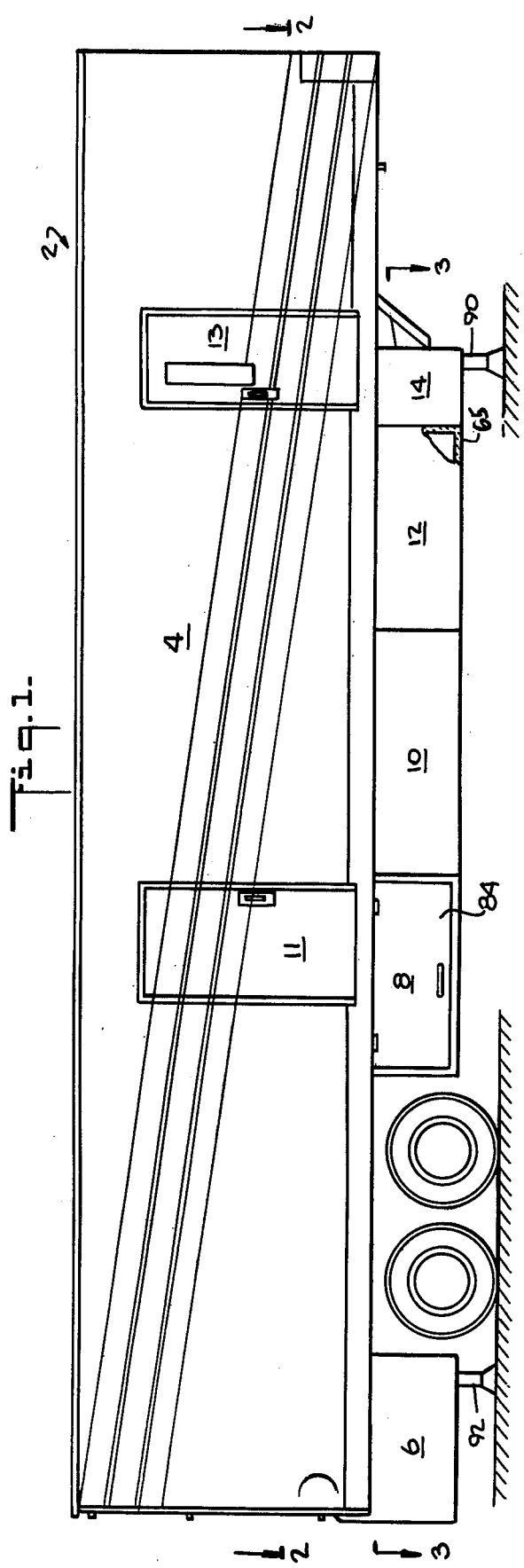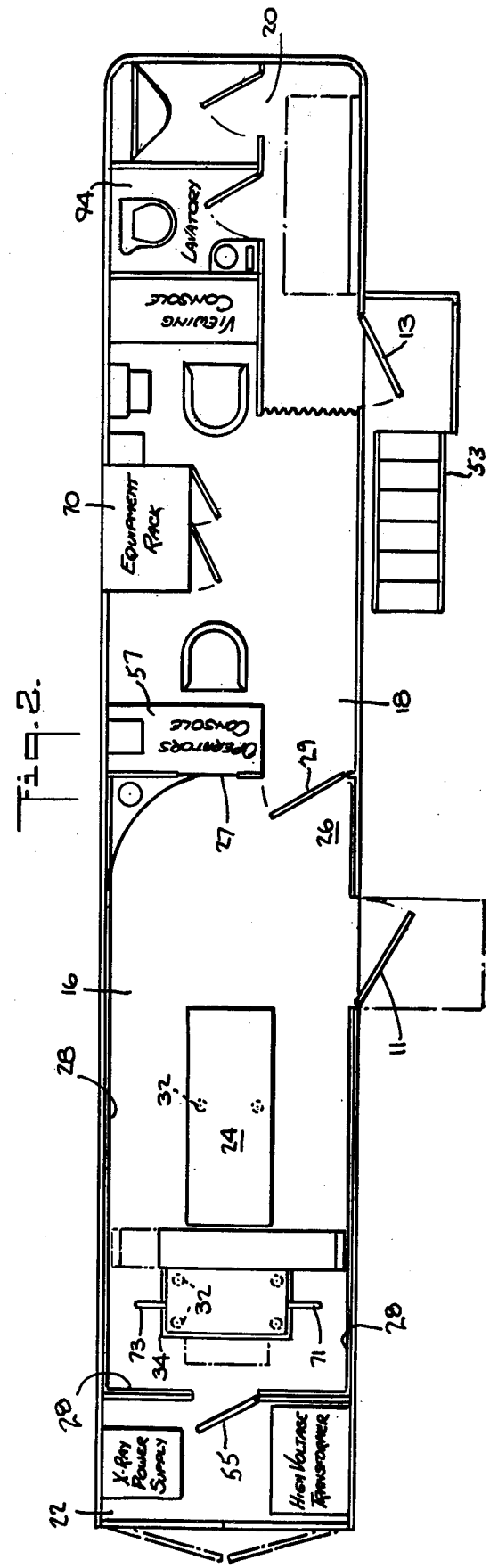

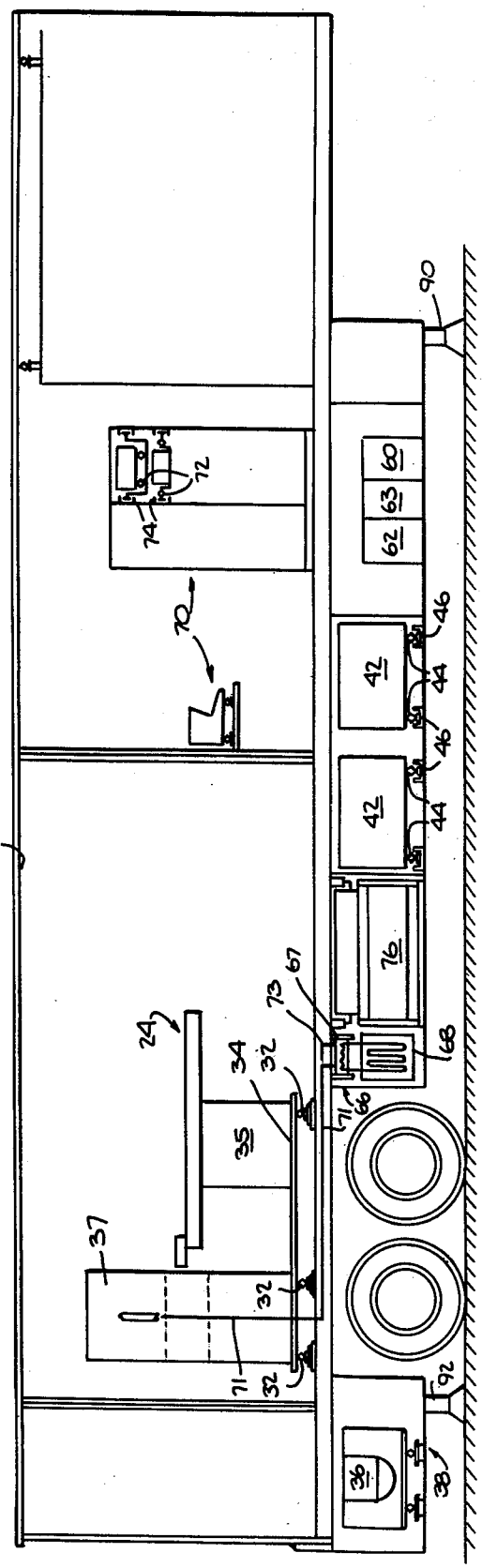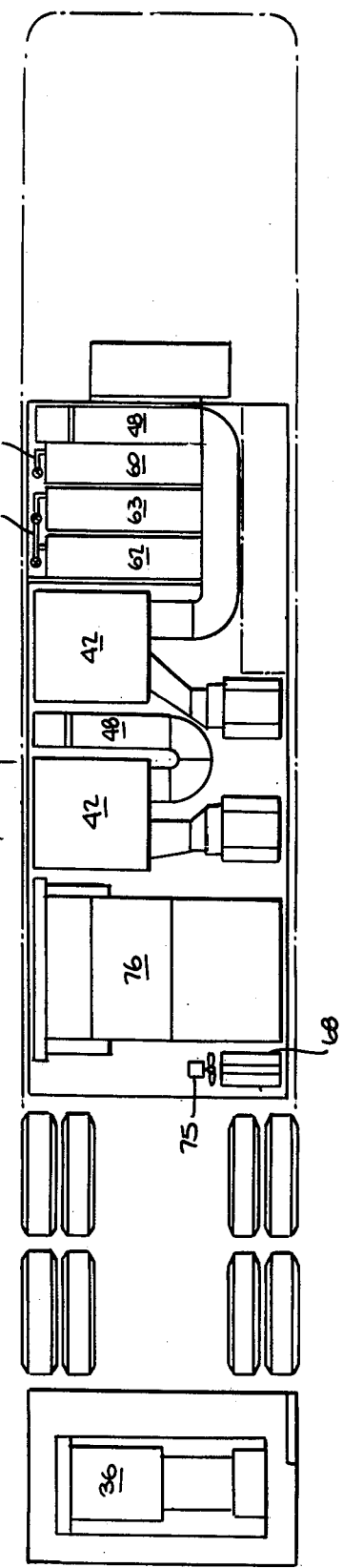

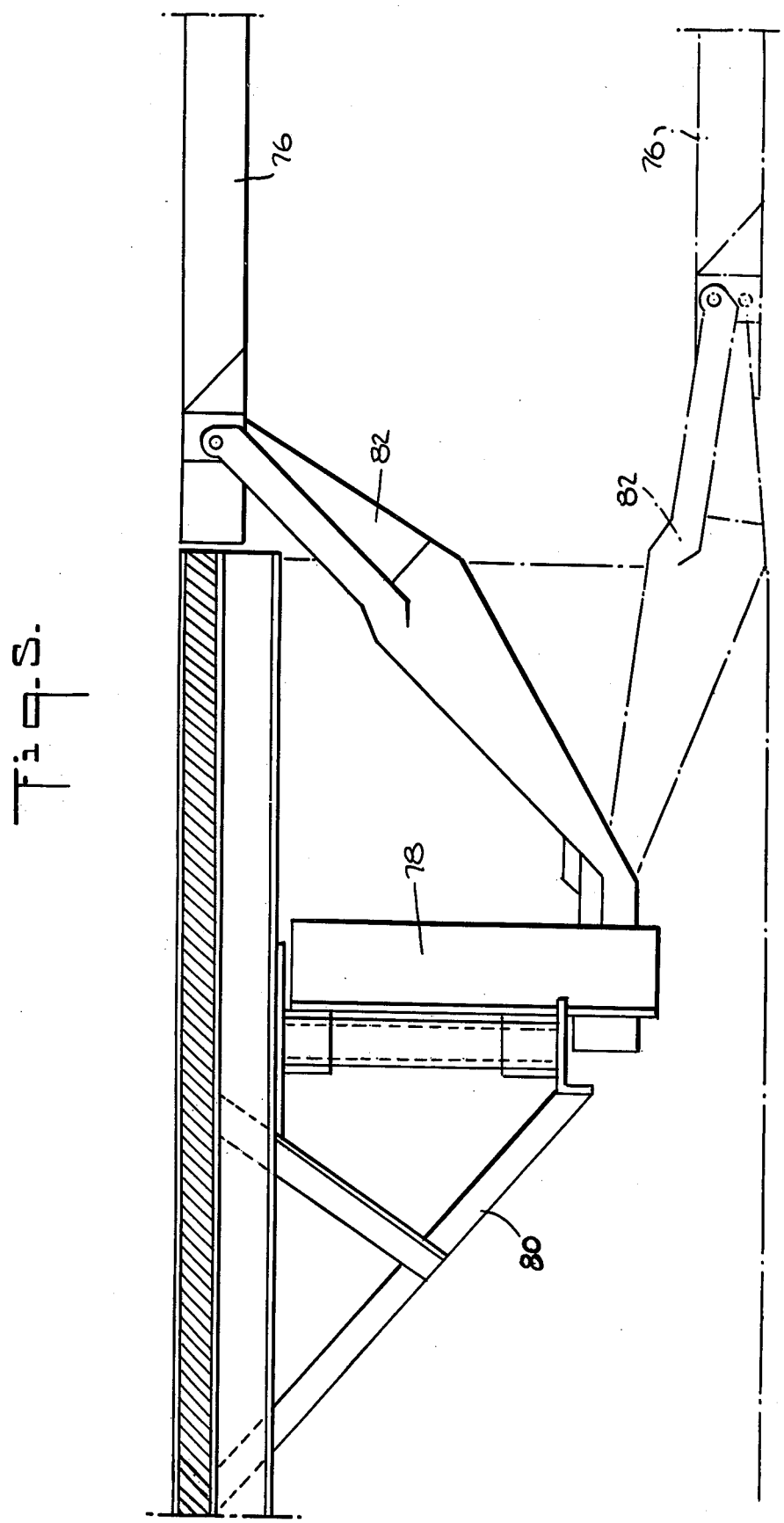

MOBILE COMPUTERIZED TOMOGRAPHY UNIT

This application is a continuation of Ser. No. 826,527 filed Aug. 22, 1977 entitled *Mobile Computerized Tomography Unit*, now U.S. Pat. No. 4,181,347 issued Jan. 1, 1980.

FIELD OF THE INVENTION

This invention relates generally to mobilized medical facilities. More particularly, the invention relates to mobilized units directed to providing medical testing facilities for use in various locations. This invention specifically provides a mobile self-contained computer tomography scanner (CT-scanner), also referred to as computed tomography and computerized axial tomography.

DESCRIPTION OF THE PRIOR ART

The value of mobilized health services has been recognized for many years. The large number of mobile chest x-ray units currently used to provide entire communities with chest x-ray services testifies to the proven value of mobile health facilities.

Recently, more ambitious mobile health service units have been put into service. Synergetics, Inc. of Gainesville, Florida has developed and put into service, a composite mobile health testing van equipped to test and record patient hematology, vision, blood pressure, X-ray, ECG, dental and various other medical aspects of an individual patient. The van is essentially a modified semi-trailer, partitioned for each testing function and provided with data processing, power generation, air conditioning and heating, plumbing and electrical sub-systems. The testing and support equipment are all provided with slide mounting means for protection from shock occurring due to travel and use.

Recently, CT-scanners have been developed which are capable of performing detailed and accurate tomographic scanning of human bodies or parts of human bodies. These scanners have great value as health testing tools, however, the high cost of each unit encourages shared operation by more than one facility. On the other hand, the weight of each unit and the support system required to render a CT-scanner self-contained have, until now, prevented mobilization of CT-scanners. Further, the questionable reliability of sensitive electronic equipment due to the shock and vibration effects of mobile travel have deterred mobilization of CT-scanners.

The current CT-scanning procedures are designed to provide maximum information for diagnosis with a minimum of exposure of the patient to the radiation necessary to effect scanning. Care is always taken to avoid repeat of the CT-scanning procedure. Under these circumstances, faulty equipment or any likelihood of unreliability of the equipment is not tolerable. Thus, CT-scanners are now located in stationary facilities where the equipment can be easily secured and maintained to insure reliability.

SUMMARY OF THE INVENTION

This invention provides a wholly or partially self-contained mobile CT-scanner capable of travel to various locations and use without assistance from additional support systems.

It is a principal object of this invention to provide a mobile CT-scanner facility with a maximum of self-containment, but which can also afford reliable CT-scanning by insulating the sensitive scanning equipment from the vibration and shock which attends both road travel and support equipment usage.

Basically the mobile CT-scanner is comprised of a conventional semi-trailer unit modified to provide a radiation shielded room for the CT-scanner gantry and patient table, and auxiliary rooms for accommodating patients, technicians and physicians and areas for the CT-scanner support equipment.

A lift is built into the vehicle to deliver non-ambulatory patients from ground level to the CT-scanner level.

Shock mounting and slide mounting is provided for the CT-scanner and support equipment such as the power generator, air conditioning unit and the data processing equipment. Power assisted stabilizers are incorporated to provide additional stability for the equipment when the unit is stationary.

DESCRIPTION OF THE DRAWINGS

The mobile CT-scanners will be better understood when considered with the following drawings wherein:

FIG. 1 is a side elevational view of the exterior of the mobile CT-scanner;

FIG. 2 is a sectional plan view through line 2—2 of FIG. 1 showing the interior floor plan of the mobile CT-scanner;

FIG. 3 is a sectional plan view through line 3—3 of FIG. 1 showing the support equipment housed in the unit subfloor;

FIG. 4 is a sectional side elevational view of the interior of the unit showing the equipment and specialized mounting means therefor; and FIG. 5 is a front sectional elevational drawing of the lift system mounted to the side of the unit.

DESCRIPTION OF THE PREFERRED EMBODIMENT

The mobile CT-scanner unit 2 of the present invention is seen in FIG. 1 having the appearance exteriorly of a conventional semi-trailer. The unit 2 is provided with a main housing section 4 and sub-floor housing areas 6, 8, 10, 12 and 14. Doors 11 and 13 provide access to the main housing section 4 of the unit 2.

As best seen in FIG. 2, the main housing section 4 is separated into the procedure room 16, control room 18, patient convenience area 20 and equipment area 22.

The procedure room 16 accommodates the CT-scanner 24 and is enclosed in radiation shielding material. Practice has shown that the CT-scanner typically generates sufficient radiation to warrant radiation protection. Protection from the radiation within procedure room 16 is provided by walls 28 and doors 11, 29 and 55 formed of 1/16 inch thick lead with plastic and wood covering and a ceiling 30, shown in FIG. 4, formed of 0.40 inch thick aluminum. The walls 28 are comprised of 16 sq. ft. plates connected by rivets and bolts to afford an allowance for vibration stresses imposed by vehicle movement and to afford ease of repair if the trailer is damaged. A technician's window 27 located between the procedure room 16 and the control room 18 is formed of lead glass, such as Nuclear-Pacific Inc. LX-55. A door 29 connects the procedure room 16 and the control room 18.

As best seen in FIG. 4, the CT-scanner 24 is mounted on shock/vibration-isolation mounts 32 and a monolithic steel plate 34. The shock/vibration-isolation mounts 32 (and also 38, 44 and 72) may be spring devices, pneumatic devices or conventional elastomeric rubber or neoprene and steel such as manufactured by Barry Wright Instrument Co. or Lord Mfg. Co. They are used either to isolate vibrations produced within the mounted device from the vehicle frame and other components or to isolate the mounted device from the vibration in the trailer frame due to shocks from traveling over the road or vibration produced by other components.

The monolithic steel plate 34 rigidly couples the patient table 35 with the scanner gantry 37. Practice has taught that a suitable plate 34 can be about ⅜ inch thick steel and can be configured in a T-shape when viewed in plan. The top of the T is approximately 88 inches across the top and 45 inches in T-depth. These dimensions are essentially the dimensions of a conventional CT-scanner gantry 37. The CT-scanner gantry 37 is rigidly mounted on the top section of the T-shaped monolithic plate 34. The overall length of the monolithic plate 34 is approximately 135 inches from the top of the T to the bottom. The patient table 35 is rigidly mounted on the portion of the T below the top crossing member. Six shock/vibration-isolation mounts 32 are located in the six corners of the T as shown in phantom on FIG. 2. The combination of mounts 32 and plate 34 provides protection from vibration for the CT-scanner and maintains registry between the CT-scanner gantry 37 and the patient table 35.

As seen in FIGS. 1 and 4, the system generator 36 is housed in subfloor compartment 6. The system generator 36 is a 45 kw. capacity gasoline or diesel unit which supplies all the power for the mobile CT-scanner unit 2. A cable and transfer switch enables utilization of either internal electric power from the generator 36 or utilization of externally supplied power. A shock/vibration mount 38, seen in FIG. 4, also mounts the generator 36 to prevent vibration from the generator unit 36 from reaching the frame of the van.

The system air conditioner 42 is housed in subfloor compartment 10 and must be capable of providing six or more tons of cooling capacity. Shock/vibration isolation mounts 44 (previously described) and a slide 46 mount the air conditioner unit 42 for vibration protection and to facilitate access for maintenance. The slides 46 (and also slides 74) are chassis-type slides, such as produced by CHASSIS-TRAK DIV. of General Devices Co., Inc., and are used to enable convenient removal of the mounted device from its enclosure for maintenance purposes. The air conditioning duct system is arranged to direct the air from the air conditioner 42 upwardly through ducts 48 to an air distributor manifold in the vehicle ceiling. Registers for both heating and air conditioning are located in each room. A return is provided for recirculating the air. Heating for the van is provided by electrical heat strips located in the air conditioner or the ducts and/or by heat exchangers using hot water supplied by the generator coolant.

A self-contained plumbing system for the mobile unit 2 is best seen in FIGS. 3 and 4. Fresh water storage tank 60, waste water tank 63 and sewage tank 62 are housed in sub-floor compartment 12. Fresh water is delivered to the procedure room 16 and lavatory by line 61. Sewage return to sewage tank 62 from the lavatory is provided by line 64. The entire compartment 12 is provided with insulation 65, as seen in FIG. 1, and afforded with provision for heating in cold weather.

As best seen in FIG. 4, a heat exchanger assembly 66 is provided to cool the oil coolant for the X-ray tube of the CT-scanner 24. An oil-to-water heat exchanger 67 and a warm water-to-air heat exchanger 68 are arranged to employ water as an intermediate coolant between the air and oil coolant. Lines 71 and 73 serve respectively to deliver oil coolant to the X-ray tube and to return warm coolant to the heat exchanger 67. As seen in FIG. 3, a fan 75 is used to blow cool air through the cold side of heat exchanger 68. Alternatively, a refrigerator type unit, such as manufactured by Oasis Mfg. Co., may be used to cool either the oil or water.

The system computer 70 for data processing is located in the control room 18. The computer 70 is a mini-computer such as manufactured by Digital Equipment Corp. or Data General Corp., and is capable of processing and displaying CT-images. The computer components are mounted on shock/vibration isolation mounts 72 and slides 74, as best seen in FIG. 4, to provide shock and vibration protection and maintenance access, respectively. For illustrative purposes only, a few of the various components of the mini-computer 70 are shown. Each component whether shown or not is mounted on shock/vibration-isolation mounts 72 and 74.

A lift 76 for non-ambulatory patients is best shown in FIG. 5. The lift 76 normally nests in subfloor compartment 8 and is powered by an electric hydraulic unit 78. Member 80 and lever 82 mount the lift platform 76 for vertical, horizontal and combined vertical and horizontal travel. In operation, the compartment door 84 opens, the lift moves horizontally outwardly, swings downwardly to the ground, receives the patient and then elevates the patient to the level of CT-scanner room floor at door 11.

A stabilizer comprised of two forward supports 90 and two rear supports 92, best seen in FIGS. 1 and 4, provides essentially rigid support for the entire unit 2 when the unit 2 is stationary. Supports 90 and 92 are housed respectively in subfloor compartments 14 and 6. The supports 90 and 92 are electrohydraulic or manual units, such as manufactured by Power-Lift Corp., and can accommodate loads of well over 30,000 pounds. When the supports 90 and 92 are employed, at least the majority of the load and, at times, the entire load is carried by the supports 90 and 92 and little or no load is on the wheels of the unit.

The patient convenience area 20 is comprised of a lavatory 94 and a dressing room 96, best seen in FIG. 2.

In operation, the CT-scanner unit 2 is designed to travel from one location to another to provide the maximum amount of health care possible in a geographic area. The mobile CT-scanner unit 2 is adapted to attach to a conventional truck cab in the same manner as any semi-trailer would connect.

The mobile CT-scanner unit 2 is transported by the cab to a location at which the actual patient scanning will occur. Upon arrival at the location, stabilizers 90 and 92 are deployed until each bear against the ground or roadbed to maintain essentially the entire weight of the unit 2 during the scanning operations. The cab is then removed from the unit 2. A stair assembly 53, which is normally carried along with the unit 2, is then arranged to facilitate entry by patients and technicians through door 13, as best seen in FIG. 2. Ambulatory patients enter the unit 2 through door 13 and dress for scanning in the patient convenience area 20. The operating personnel including both physicians and technicians occupy the control room 18 except when tending patients in the convenience room 20 or the procedure room 16. Each patient, after being interviewed and examined, waits in the patient area 20 until it is their turn to be scanned. When the patient is ready for scanning, a technician leads the patient from the patient convenience room 20 through the control room 18 to the door 29 and into the procedure room 16. The patient is placed on the scanner table 35 and the table 35 is moved into alignment with the gantry 37. The attendants leave room 16, close all doors and conventional CT-scanning then proceeds while the mini-computer equipment 70 reads and records the data being transmitted from the scanner. An operator at console 57 monitors the scanning procedure. The door 29 is always closed as is door 11 and the transformer room door 55 when scanning is in progress.

The procedure for accommodating the non-ambulatory patients differs from the procedure for ambulatory patients in that the lift 76 is deployed from the nested position and lowered until it is flat on the ground. The non-ambulatory patient is placed on the lift 76, usually with an attendant, and the lift 76 is elevated so that the lift surface 76 is in alignment with the floor 26 of the procedure room 16 at the door entrance 11. The patient is taken through the door 11, placed on the scanner table 35 and aligned with the scanning mechanism. The attendants leave room 16, all the doors to room 16 are closed and the scanning begins. During the scanning, an operator seated at the operator's console 57 observes the scanning procedure through the lead glass window 27 and the mini-computer 70 records the data being delivered by the scanner.

The arrangement of the scanner gantry 37 and the scanner table 35 and components of the mini-computer 70 on the shock/vibration isolation mounts provides protection from vibration which attends vehicle travel and generator operation. Thus, scanning is performed reliably and rapidly for extended periods of time. The monolithic plate 34 insures that during travel of the van and during the occasions when the generator 36 is running, registry between the scanner gantry 37 and the scanner table 35 is not disturbed.

Further reliability is provided by the heat exchangers 66 and 73 which insure that the scanner X-ray tube is maintained at the proper temperature.

The power for the scanner and mini-computer along with the power for the support systems can all be provided by the generator 36. Thus, self-containment of the unit 2 is facilitated by the existence of the generator 36 and the reliability of the equipment is insured by insulating the equipment from both the shock attending the operation of the generator 36 and travel of the vehicle.

What is claimed is:

1. A mobile computerized tomography unit comprising:
   a vehicle trailer;
   a CT-scanner gantry and patient table;
   means for mounting the CT-scanner gantry and patient table as a unit and to prevent shock vibration from being transmitted to the CT-scanner gantry and patient table during travel of the mobile unit;
   a mini-computer system for display and data processing of the CT-scanner mounted in the trailer;
   means for mounting the mini-computer components to prevent shock vibration from being transmitted to each mini-computer component;
   means for rigidly supporting the unit when the van is stationary.

2. A mobile computerized tomography unit as in claim 1 further comprising an air conditioning unit mounted in the vehicle.

3. A mobile computerized tomography unit as in claim 1 further comprising:
   a monolithic plate to mount the CT-scanner gantry and patient table as a unit;
   an elastomeric mount for the CT-scanner gantry and patient table;
   elastomeric mounts for the mini-computer components; and
   a slide for mounting the elastomeric mounts for the mini-computer components, which slide allows the mini-computer components to be removed from the computer component enclosure.

4. A mobile computerized tomography unit as in claim 3 wherein the means for mounting the CT-scanner gantry and the patient table is a T-shaped monolithic plate and the CT-scanner gantry is rigidly mounted on the cross member of the T-shaped monolithic plate, the CT-scanner table is mounted on the member of the T-shaped monolithic plate extending from the cross member of the T and further comprising a shock/insulation vibration mount supporting each of the six corners of the T-shaped monolithic plate.

5. A mobile computerized tomography unit as in claim 4 further comprising supports which are housed within the vehicle during travel of the vehicle and means for deploying the supports from the vehicle to the ground, whereby the major portion of the weight of the vehicle is supported by said supports when the vehicle is stationary.

* * * * *